United States Patent
Feydo et al.

(10) Patent No.: US 10,466,209 B2
(45) Date of Patent: Nov. 5, 2019

(54) LOW-POWER WIRELESS DEVICE FOR ASSET-INTEGRITY MONITORING

(71) Applicant: SENSOR NETWORKS, INC., Boalsburg, PA (US)

(72) Inventors: Mark Feydo, Reedsville, PA (US); Jeffrey Anderson, Lewistown, PA (US); James Barshinger, State College, PA (US)

(73) Assignee: SENSOR NETWORKS, INC., Boalsburg, PA (US)

( * ) Notice: Subject to any disclaimer, the term of this patent is extended or adjusted under 35 U.S.C. 154(b) by 112 days.

(21) Appl. No.: 15/841,040

(22) Filed: Dec. 13, 2017

(65) Prior Publication Data

US 2018/0164258 A1 Jun. 14, 2018

Related U.S. Application Data

(60) Provisional application No. 62/433,424, filed on Dec. 13, 2016.

(51) Int. Cl.
*H03M 1/02* (2006.01)
*H04B 11/00* (2006.01)
(Continued)

(52) U.S. Cl.
CPC ........... *G01N 29/265* (2013.01); *G01B 17/04* (2013.01); *G01M 3/24* (2013.01); *G01M 3/243* (2013.01);
(Continued)

(58) Field of Classification Search
CPC ........ G01B 17/04; G01M 3/24; G01M 3/243; G01N 29/02; G01N 29/04; G01N 29/22;
(Continued)

(56) References Cited

U.S. PATENT DOCUMENTS

| 4,290,308 A | 9/1981 | Dau |
| 4,803,638 A * | 2/1989 | Nottingham ........... G01N 29/22 702/36 |

(Continued)

FOREIGN PATENT DOCUMENTS

CN 104181280 * 12/2014

OTHER PUBLICATIONS

International Search Report for PCT/US17/66178 dated Feb. 20, 2018.
(Continued)

*Primary Examiner* — Jacques M Saint Surin
(74) *Attorney, Agent, or Firm* — Fisherbroyles LLP

(57) ABSTRACT

A sensor for ultrasonically measuring a portion of a structure, the sensor comprising: a transducer for converting an analog transmit signal to an ultrasonic transmit signal, and for converting an ultrasonic reflected signal to an analog reflected signal; a housing integrated with the transducer and containing at least: a processor; a wireless data transmitter for transmitting wirelessly a data signal from the processor; a transmit and receive circuit for transmitting an analog transmit signal to the transducer in response to a transmit trigger from the processor, and for receiving an analog reflected signal from the transducer; an A/D converter for digitizing only a portion of the analog reflected signal in response to a sample trigger from the processor; a battery to supply power to the processor, the wireless data transmitter, the transmit and receive circuit, and the A/D converter; memory operatively connected to the processor and configured to instruct the processor to execute the following steps: repeatedly triggering the transmit and receive circuit and the A/D converter to obtain a digitized composite signal through time-equivalent sampling; processing the digitized composite reflected signal to generate an A-scan signal; and wire- (Continued)

lessly transmitting the data signal based on the A-scan signal for transmission to a discrete collection device.

24 Claims, 4 Drawing Sheets

(51) Int. Cl.
    *G01M 3/24*     (2006.01)
    *G01B 17/04*     (2006.01)
    *G01N 29/02*     (2006.01)
    *G01N 29/04*     (2006.01)
    *G01N 29/22*     (2006.01)
    *G01N 29/34*     (2006.01)
    *G01N 29/36*     (2006.01)
    *G01N 29/40*     (2006.01)
    *G01N 29/44*     (2006.01)
    *G01N 29/06*     (2006.01)
    *G01N 29/24*     (2006.01)
    *G01N 29/265*     (2006.01)

(52) U.S. Cl.
    CPC .............. *G01N 29/02* (2013.01); *G01N 29/04* (2013.01); *G01N 29/043* (2013.01); *G01N 29/0645* (2013.01); *G01N 29/22* (2013.01); *G01N 29/2481* (2013.01); *G01N 29/34* (2013.01); *G01N 29/36* (2013.01); *G01N 29/40* (2013.01); *G01N 29/44* (2013.01); *H03M 1/02* (2013.01); *H04B 11/00* (2013.01); *G01N 2291/0258* (2013.01); *G01N 2291/044* (2013.01)

(58) Field of Classification Search
    CPC ........ G01N 29/34; G01N 29/36; G01N 29/40; G01N 29/2481; G01N 29/265; G01N 2291/0258; G01N 2291/044; H03M 1/02; H04B 11/00
    USPC .......................................................... 73/622
    See application file for complete search history.

(56) References Cited

U.S. PATENT DOCUMENTS

| | | | |
|---|---|---|---|
| 5,723,791 A | 3/1998 | Koch et al. | |
| 5,951,479 A * | 9/1999 | Holm | G01S 7/52046 600/443 |
| 5,963,882 A | 10/1999 | Viertl et al. | |
| 2004/0035208 A1* | 2/2004 | Diaz | G01N 29/024 73/597 |
| 2008/0314153 A1* | 12/2008 | Langlois | G01N 29/069 73/606 |
| 2015/0194039 A1* | 7/2015 | Martin | G08B 21/182 340/632 |
| 2016/0274065 A1 | 9/2016 | Barshinger et al. | |

OTHER PUBLICATIONS

International Preliminary Report on Patentability for International Application No. PCT/US17/66178 dated Jun. 18, 2019.

* cited by examiner

LOW-POWER WIRELESS DEVICE FOR ASSET-INTEGRITY MONITORING

REFERENCE TO RELATED APPLICATION

This application is based on U.S. Provisional Application No. 62/433,424 filed on Dec. 13, 2016, which is hereby incorporated by reference.

FIELD OF INVENTION

This invention relates to a device for ultrasonically monitoring the condition and integrity of pipes and/or other structures or assets, such as those used in the oil and gas and power generation industries using an improved, low-power and low-cost architecture.

BACKGROUND

Wall thickness and the presence of defects such as cracks are important factors in determining the fitness-for-service of structures such as above- and below-ground pipes and tanks, including bulk material and weldments. When a pipe is in operation, it can be subject to corrosion and/or erosion due to the content, flow and/or environmental conditions inside or outside of the pipe. Cracks can form and propagate due to the presence of manufacturing defects, creep, thermal cycling, fatigue and environmental conditions causing defects such as high-temperature hydrogen attack (HTHA), stress-corrosion cracking, etc. Corrosion and/or erosion results in the reduction in wall thickness, which can reach a point at which operating conditions becomes unsafe, considering that the pipe can be pressurized and may contain hazardous or flammable materials. Likewise formation and propagation of cracks, in welds for instance, can cause similar unsafe conditions. A failure may cause catastrophic consequences such as loss of life and environmental damage, leaking pipes, in addition to the loss of the use of the asset, and any corresponding costs associated with repair, loss of capacity and revenue loss.

Ultrasonic non-destructive evaluation (NDE) techniques are commonly used for evaluating the integrity of industrial components. In the case of measuring wall thickness reduction due to erosion/corrosion, the traditional process involves using a portable handheld instrument and ultrasonic transducer (probe) to measure the wall thickness. The instrument excites the probe via an electrical pulse, and the probe, in turn, generates an ultrasonic pulse which is transmitted through the structure. The probe also receives an echo of the ultrasonic pulse from the structure, and converts the pulse back into an electrical signal. The ultrasonic pulses that are transmitted into and received from a structure are used to determine the relative position of the surfaces (i.e. thickness) of the structure wall. More specifically, by knowing the travel time of the ultrasonic pulse from the outer wall to the inner wall and back ($\Delta T$) and acoustic velocity (V) of the ultrasonic pulse through the material of the structure (through calibration or just initialization), a wall thickness (d) can be calculated—i.e. $d = \Delta T \cdot V/2$. There are many variants of these two basic descriptions of ultrasonic thickness gauging and flaw detection that are known to skilled practitioners of ultrasonic nondestructive evaluation.

These approaches require an operator to manually position a probe on the wall of the asset to take a reading. Not only does this necessitate the operator manually taking each reading, but also the measurement location must be accessible, which can be challenging and costly. For example buried pipelines require excavation to access, insulated pipe requires costly removal of the insulation, offshore assets require helicopter or boat access, and elevated vessels requiring scaffolding or crane access. While the measurement is relatively simple, the cost of access (scaffolding, excavation, insulation removal, etc) is often much higher than the cost of measurement. Moreover, the operator is often subjected to hazardous conditions while taking the readings. Furthermore, to obtain trending data with thickness resolution of 0.001" or better requires that the transducer be placed in the same exact location for consistent readings at regular time intervals. This is difficult and often impractical especially when the data-capture rate needs to be frequent. Variations in operator and/or equipment tend to skew the quality and integrity of the measurement data.

One approach for avoiding some of the aforementioned problems is to use installed sensors/systems for asset-condition or asset-integrity measurement. The sensors are permanently or semi-permanently installed on the asset and can take advantage of features such as wireless data transmission to avoid costly wiring installations. Automated systems require no operator to be in the vicinity of the asset and can stream data to a control room or to an operator's desk. Current state of the art devices/systems have been shown to be useful and commercially successful for permanently monitoring structures using ultrasound.

While current state of the art devices are useful and valued for corrosion monitoring, Applicants have identified two major shortcomings in that current devices are high cost and require large amounts of power to operate. The large amount of power requires large, lithium ion batteries (often D size cells) to meet required battery life requirements of 5-10 years with a 1/day measurement cycle. These large lithium ion batteries negatively impact cost and have safety and shipping issues due to the large volume of lithium. Furthermore, the volume of the batteries limits the amount of miniaturization that can be accomplished.

There are several factors that drive the power and cost of current state of the art systems. The first involves the relatively high frequencies used in ultrasonic NDT. Typical thickness gauging is carried out between 1 and 10 MHz to achieve the proper balance between penetration power, beam characteristics and near-surface resolution. According to Nyquist's theorem, the digital sampling of signals of frequency F, must be at a rate greater than 2F to properly represent the signal. As the signals used in NDT are typically pulses, the bandwidth of those signals and the desire for accurate timing measurements drives the requirement of even higher sampling rates, in the range of 5 to 10× the center frequency of the transducer. Sampling rates of 40 to 100 MSPS are commonly used. This requirement drives the system architecture to be somewhat complex, requiring a high-speed digitizer, and usually FPGA (field programmable gate array) to handle the high-speed signals. The additional components increase power consumption during signal acquisition, require more complicated power supply architectures to handle the multiple voltages necessary for the circuit, and increases circuit board size and component cost.

Applicants have also identified a second factor, particularly for installed sensor systems with wired transducers is the cost of long cabling, connectors, installation and signal degradation. Cabling with suitable electrical characteristics and appropriate for the harsh environments can cost several dollars per foot. Coaxial connectors are also expensive from both a part and assembly cost. Cable and connector costs can easily exceed $50-100. The high-frequency signals that connect the probe to its ultrasonic instrument, degrade considerable over distances as short as 8 meters. Labor costs for the type of industrial wiring and conduits at Oil & Gas or Power Plant sites often renders wiring too costly to be practical especially for semi-permanent installations.

A third factor is the choice of using mesh network topologies. In a mesh network, devices are not only responsible for handling their own data, but are also responsible for repeating messages for neighboring devices. As such, devices on a mesh network must always be connected to the network to be ready to receive, transmit, or repeat a message. Current mesh network protocols based on the 802.15.4 standard are often deployed on the unlicensed 2.4 GHz Industrial, Scientific and Medical (ISM) band. Range of such networks are usually less than 200 meters, often requiring extra repeater nodes to achieve connectivity of devices over a large facility. Sometimes one or more repeater nodes are required for each operating sensor to achieve the necessary wireless coverage.

To address these shortcomings, Applicants have designed a novel device for implementing a permanently installed thickness gauge that is wireless, low power, miniature and only requires single small battery to run for significant amounts of time (e.g., 5-10 years).

SUMMARY OF INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

Applicants recognize that the power requirements of a sensor may be decreased significantly by avoiding the use of a discrete A/D converter and associated field programmable gate array (FPGA). Such devices increase significantly the power and/or circuit capacitance of the sensor. Applicants recognize further that such components can be eliminated if the sensor relies on the relatively low-power A/D converter that is typically integrated with a digital processor, instead of a discrete A/D converter. Although the integrated A/D converter is not as fast as a discrete A/D converter, and, thus may not facilitate the processing speeds required for real-time signal processing, Applicants have found that the slower A/D converter can perform time-equivalent sampling of multiple signal acquisitions to generate a composite signal with higher effective sampling rate. While time-equivalent sampling of multiple signals may not be effective with manual probes because of the difficulty in generating multiple signals without variation, the permanent/semi-permanent nature of the sensors of the present invention and their ability to generate multiple signals rapidly without substantial variation renders them ideal for time-equivalent sampling.

There are a number of important benefits flowing from a sensor using time-equivalent sampling, and the elimination of power-consuming components such as the A/D converter and FPGA. First, the elimination of these components lowers the peak power consumption of the sensor as a whole. Not only does this allow the use of smaller batteries, but also this configuration lowers the overall capacitance of the sensor as a whole. Lowering the capacitance is critical in making the sensor intrinsically safe for hazardous locations. Second, the elimination of components reduces the size of the device which renders it more manageable. Third, fewer components equate to lower cost. Still other benefits will be known to those of skill in the art in light of this disclosure.

Accordingly, in one embodiment, the invention relates to a sensor configured for ultrasonically measuring a portion of a structure using time equivalent sampling. The sensor comprises: a transducer for converting an analog transmit signal to an ultrasonic transmit signal, and for converting an ultrasonic reflected signal to an analog reflected signal; a housing integrated with said transducer and containing at least: a processor; a wireless data transmitter for transmitting wirelessly a data signal from said processor; a transmit and receive circuit for transmitting an analog transmit signal to said transducer in response to a transmit trigger from said processor, and for receiving an analog reflected signal from said transducer; an A/D converter for digitizing only a portion of said analog reflected signal in response to a sample trigger from said processor; a battery to supply power to said processor, said wireless data transmitter, said transmit and receive circuit, and said A/D converter; memory operatively connected to said processor and configured to instruct said processor to execute the following steps: repeatedly triggering said transmit and receive circuit and said A/D converter to obtain a digitized composite signal through time-equivalent sampling; processing said digitized composite reflected signal to generate an A-scan signal; and wirelessly transmitting said data signal based on said A-scan signal for transmission to a discrete collection device.

DETAILED DESCRIPTION

Figure 1B:
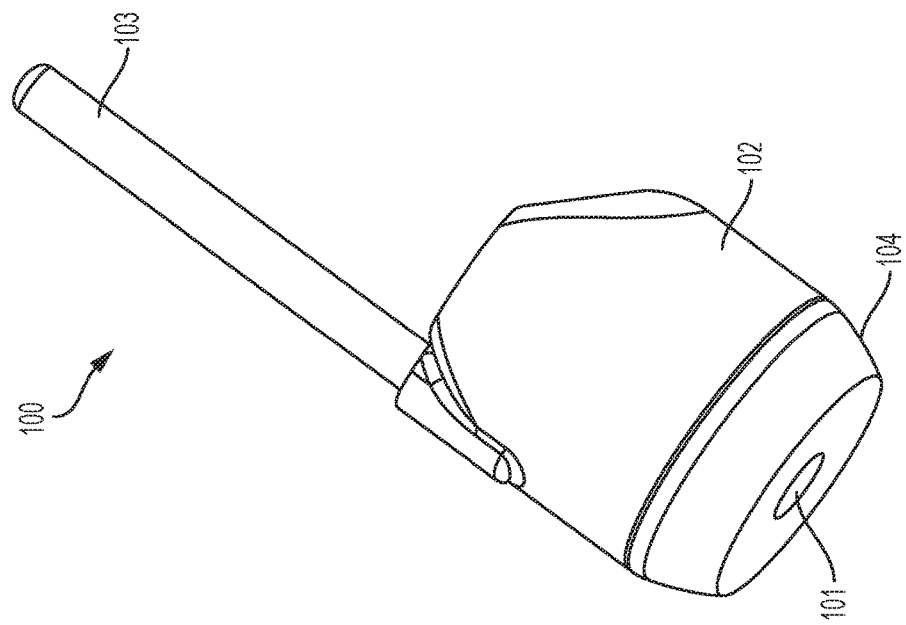
FIGS. 1A and 1B show a side view and perspective view, respectively, of one embodiment of a sensor of the present invention in which the DSI is integrated with the transducer.

Referring to FIGS. 1A, 1B, 2, and 3, a perspective view and a schematic block diagram of one embodiment of the sensor 100 of the present invention is shown. The sensor is configured for measuring ultrasonically a portion of a structure. The sensor comprises a transducer 101 for converting an analog transmit signal to an ultrasonic transmit signal, and for converting an ultrasonic reflected signal to an analog reflected signal. The sensor also comprises a housing 102, which, in this embodiment, is integrated with the transducer to form a unitary package. The sensor also comprises at least the following contained in the housing: a processor 304; a wireless data transceiver 309 for transmitting wirelessly a data signal from the processor 304; a transmit and receive circuit 301 for transmitting an analog transmit signal to the transducer in response to a transmit trigger from the processor, and for receiving an analog reflected signal from the transducer; an A/D converter 303 for digitizing only a portion of the analog reflected signal in response to a sample trigger from the processor; and a battery 310 to supply power to the processor.

In one embodiment, the wireless data transmitter, transmit and receive circuit, A/D converter; and memory 308 are operatively connected to the processor and configured to instruct the processor to execute the following steps: repeatedly triggering the transmit and receive circuit and the A/D converter to obtain a digitized composite signal through time-equivalent sampling; processing the digitized composite reflected signal to generate an A-scan signal; and wirelessly transmitting the data signal based at least in part on the A-scan signal for transmission to a discrete collection device.

Figure 1A:
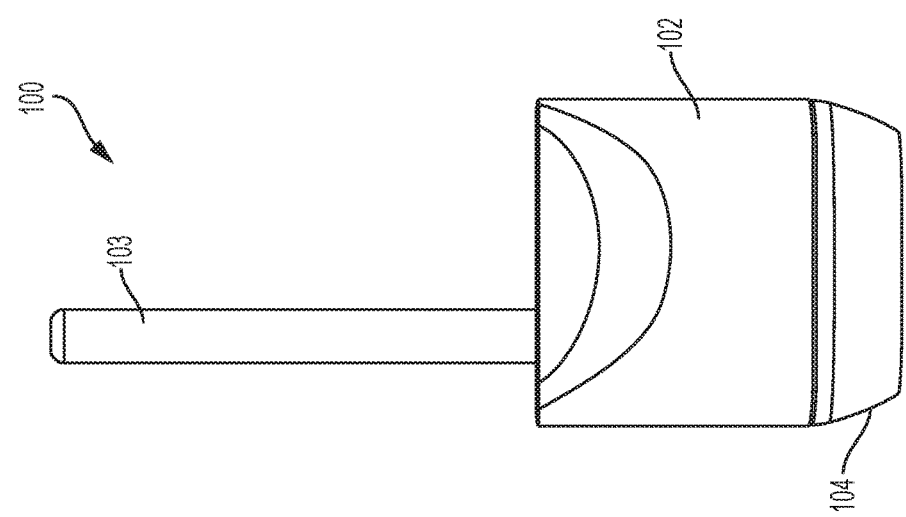
Figure 3:
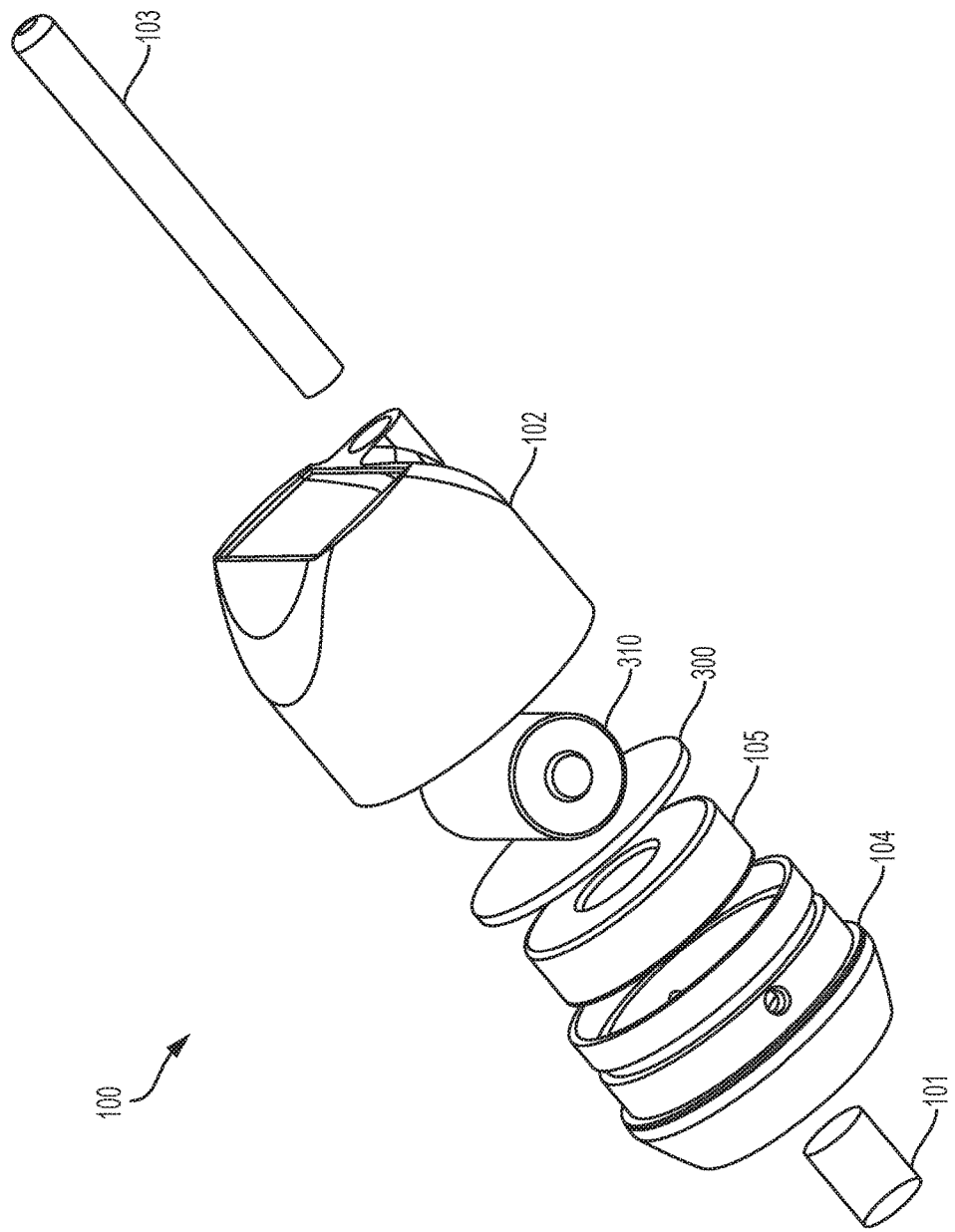
FIG. 3 shows an exploded view of the sensor of FIG. 1.

The sensor of the present invention is similar, in many respect to that disclosed in 2016/0274065, hereby incorporated by reference in its entirety, including those references incorporated by reference therein, e.g., U.S. application Ser. No. 14/839,694 (thus also incorporated by reference herein). One notable difference in the present application is the explicit integration of the digital sensor interface (DSI) 300 with the transducer to form a compact sensor package 101 as shown in FIGS. 1A, 1B & 3. Another difference is the use of time-equivalent sampling to reduce components, size and power requirements as mentioned above.

In one embodiment, the device is constructed in a unitary housing that contains the relevant physical components of the device in an environmentally-sealed configuration. The housing may be monolithic or composed of multiple components. In one embodiment, as shown in FIGS. 1A and 1B, the housing is composed of at least two parts, a bottom component (104) and top component (102). The housing can be fabricated of any rigid, thermally stable material, including, for examples, metal, such as aluminum or stainless steel, or plastic, such as polycarbonate. Further, the two or more housing components may be of the same or different materials.

The shape of the housing can vary dependent on the application, for example, it can be bulbous, elongated, rectilinear or even have a rigid cable extender for high temperature applications. In one embodiment, shown in FIGS. 1A and 1B, the bottom housing component is generally cylindrical and has a central bore in which an ultrasonic transducer (101) is mounted as shown in FIG. 1B. In an alternative embodiment, the housing is elongated to space temperature-sensitive electronics (e.g. processor, memory, etc.) away from the transducer for high temperature applications. The transducer (101) in a one embodiment of the invention is rigidly glued within the lower housing and the exit surface is coplanar with the bottom of the housing. In an alternative embodiment, the transducer is spring loaded within the central bore of the housing to bias the sensor outward, thereby achieving some degree compliance between the part under test and the ultrasonic beam's exit surface of the transducer.

In one embodiment, the sensor also comprises a mechanism for connecting the sensor to the asset to be monitored. In this way, the sensor is a "permanently installed connector." Permanently installed connectors are distinct from mobile or hand held sensors in that they are secured to the asset being tested and are not subject to movement between scans. It should be understood that the term permanently does not preclude the sensor from being releasable from the asset. Various configurations are possible including, for example, a magnet, adhesive, clamps/brackets, and tape. In the embodiment shown in FIG. 3, the housing has a ring shaped recess that is coaxial with the central bore for which a ring shaped magnet (105) can be mounted. The magnet should be proximate to the outer surface such that significant mechanical attachment force can be exerted between the magnet and the component under test. For example, in this embodiment, this ring shaped recess extends to within 0.01" to 0.1" of the outer surface. The integral magnet (105) mounted within the lower housing is of rare earth type and is used for mechanically mounting the transducer to a ferromagnetic structure (such as to a steel pipe). The magnet material can be chosen to be any of several grades as appropriate for the application. In an ideal embodiment, the material designated N42SH is used due to its high field strength and elevated temperature performance. Alternatively, additional mechanical attachment hardware may be integrated with the housing base for applications in which magnetic attachment is impractical.

The top or upper housing encloses the circuitry and battery of the device. For example, in one embodiment, the bottom housing also has provisions such as attachment points for one or multiple circuit boards to accommodate the electrical circuit (300) and a battery holder.

In one embodiment, the sensor comprises battery 310 to eliminate the need for wired power and to generate the various DC voltages required by the circuit and radio, 309, for transmitting and receiving information, data and/or signals over a cellular network. Suitable batteries are well known and include those used for voice/cell phone communications. Based on the disclosed architecture, sampling scheme and available radio technologies, it is anticipated that 10-year battery life using a single AA lithium cell is possible. In one particular embodiment, the battery (310) is a single ⅔rd size AA lithium battery, or a single AA size lithium battery, although other battery configures are possible. To accommodate a removable battery, the housing may have a detachable cover to access and replace the battery.

The upper housing may also have a mounting point for an external antenna. The antenna can be permanently mounted to the housing, or the antenna port can be a coaxial connector such as an SMA to accommodate a removable or remote antenna. In another embodiment, the antenna is mounted internally and may be integrated onto or attached to one of the circuit boards. In this case, the upper housing will designed with appropriate materials to be transparent to the RF such that the housing also serves as a ray dome for the antenna.

The transducer configuration may vary according to the application. For example, the transducer can be (1) a contact transducer having the piezoelectric element and a single or multiple matching layers between the element and the acoustic port of the transducer; (2) a delay-line transducer, having a delay line interposed between the transducer element and the acoustic output; (3) a dual-element transducer having two delay lines with separate transmit and receive elements; (4) a linear or area array of multiple (16 or 32 or xx) single-element contact transducers; or (5) a remote transducer (e.g., a high-temperature ultrasonic transducer) having a short, rigid coaxial cable extending from the transducer to an upper housing in which the temperature-sensitive electronics are housed. The choice of transducer is governed by the testing application and it is envisioned that the disclosed device will be offered in several models with different transducer choices to accommodate various test object and environmental conditions.

Prior to disclosing the electrical aspects of the invention, it is necessary to first describe an important functional aspect of the digital sampling scheme of one embodiment of the invention. As mentioned in the background, it is necessary to sufficiently sample an ultrasonic signal in order to represent the signal properly in the digital domain to then support further digital signal processing of the signals such as echo timing measurements. In modern ultrasonic instruments, this is usually accomplished with a high speed digitizer, in the range of 40 to 100 MSPS to support the typical ultrasonic probe frequencies of 1-10 MHz. Unfortunately, the A/D converters currently integrated into state of the art microcontrollers tend not to be fast enough to directly digitize signals at such high speeds, resulting in the need for additional components (A/D converters, field-programmable gate array (FPGA)) which drives system cost, complexity and power consumption.

The scheme of the present invention uses the relatively low speed A/D converters available in common microcontrollers to sample the signal such that the electrical circuit is simpler, lower cost, and lower power than in current devices. In an exemplary embodiment, the digitizer rate available is in the range of 1-4 MSPS resulting in an under-sampled signal. To raise the sampling rate to acceptable levels, in one embodiment, the sensor has an additional control on the timing (or triggering) of the ultrasonic transmission, such that the transmission can be deliberately delayed some fraction of the sampling rate. On repeated transmissions and receptions, the transmission delay is varied, such that an equivalent higher sampling rate can be accomplished.

For example, a base digitization rate of 4 MSPS can be effectively increased to 40 MSPS by taking a total of 10 transmissions/receptions, each transmission being delayed by 25 ns from the previous transmission. Specifically, if that transmission zero (T0) is defined as the first transmission/reception, then the second T/R is made with a delay of 25 ns, the third TR with a delay of 50 ns and so on. After all ten T/Rs have occurred, the ten collected waveforms are assembled into a composite waveform that is effectively sampled at 40 MSPS.

If individual collected data points are represented as $T_{ji}$ where "j" denotes the sample position in the waveform collected at 4 MSPS (j=0, 1, 2, 3 . . . 199) and "i" denotes the time delayed transmissions (i=0, 1, 2 . . . 9 in this example) and, then the composite waveform will be digitized at 40 MSPS and composed of the 2000 samples as follows:

$T_{00}, T_{01}, T_{02}, T_{03}, T_{04}, T_{05}, T_{06}, T_{07}, T_{08}, T_{09}, T_{10}, T_{11}, T_{12}, T_{13}, T_{14}, T_{15}, T_{16}, T_{17}, T_{18}, T_{19}, T_{20}, T_{21}, T_{22}, \ldots T_{199,9}$ This process as known as Equivalent-Time sampling (ETS). Alternatively, this process is also called Time-Equivalent Sampling (TES).

A requirement of ETS is that the signal is unchanging between transmissions as the same signal pattern must be sampled on multiple transmissions. In the case of traditional ultrasonic NDE applications this is usually not the case as the transducer is usually being scanned, thus one cannot guarantee that the waveform is unchanging between transmissions. Thus, ETS is not suitable for conventional UT instruments. However, Applicants recognize that for an installed sensor application, in which the transducer is permanently attached, the use of ETS is not only possible, but is highly beneficial from the standpoint of the resulting simpler system architecture which in turn results in lower system cost and significantly reduced power consumption.

Due to the use of ETS, the resulting device architecture, in one embodiment, becomes simply a microcontroller with various peripheral components to create the desired functionality of the system. The microcontroller governs the function of the device and has embedded software to perform such functions as data acquisition (digitization), signal processing and measurement of the UT data, power management, and control of the radio transceiver.

Figure 4:
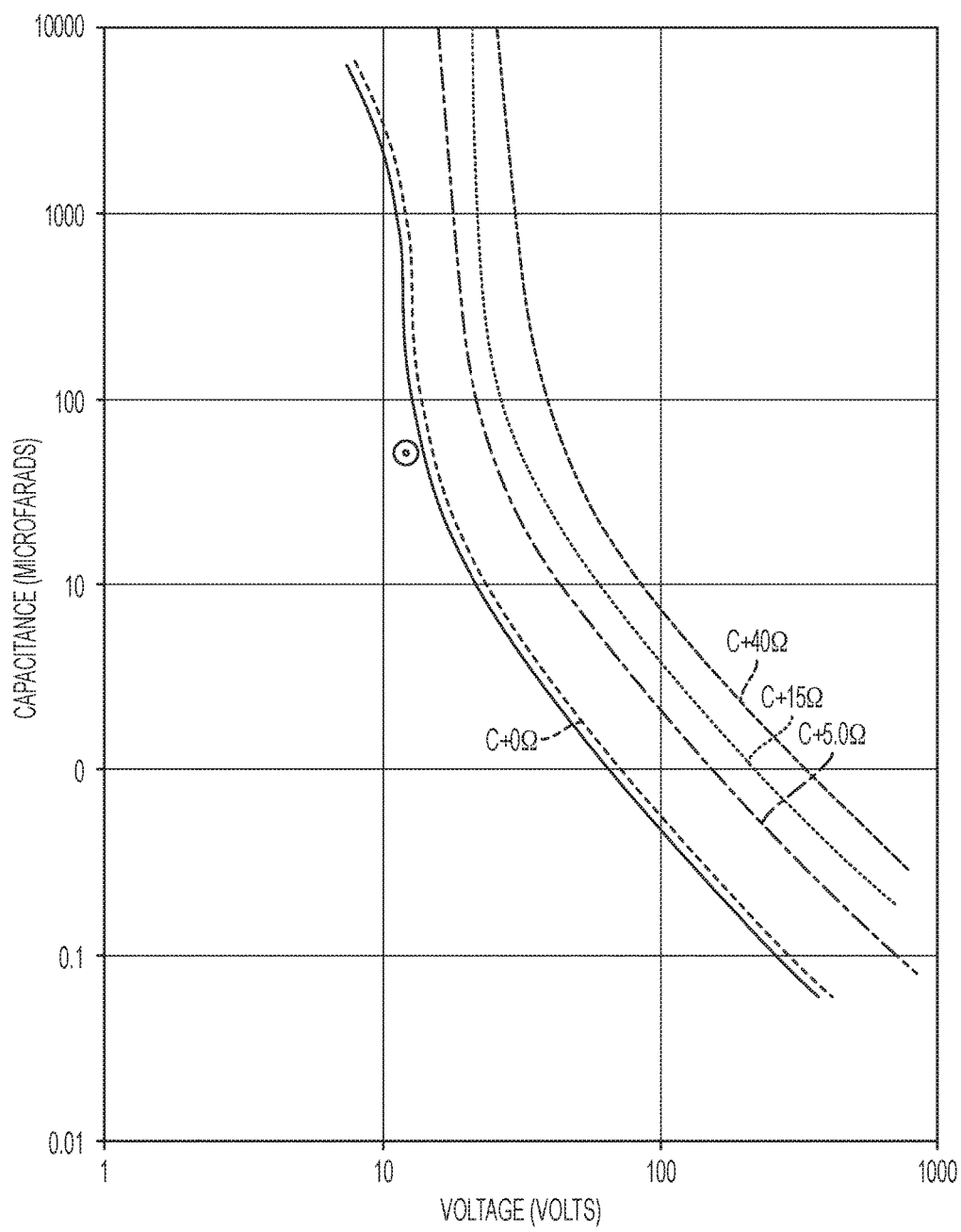
FIG. 4 shows a capacitive ignition curve for the evaluation of intrinsically safe circuits.

There are a number of important benefits flowing from a sensor using time-equivalent sampling, and the elimination of power-consuming components such as the A/D converter and FPGA. The elimination of these components lowers the peak power consumption of the sensor as a whole. Not only does this allow the use of smaller batteries, but also this configuration lowers the overall capacitance of the sensor as a whole. Lowering the capacitance is critical in making the sensor intrinsically safe for hazardous locations. Intrinsic safety is a protection technique for safe operation of electrical equipment in hazardous areas by limiting the energy, electrical and thermal, available for ignition. In one embodiment, the total capacitance of the electrical component contained within the housing for a given operating voltage is less than that as indicated in the plot of FIG. 4. Specifically, FIG. 4 shows the relationship between capacitance and voltage for group I apparatus, although different curves are readily available for other situations. What is significant is that if a small series resistor is added to the circuit, the voltage of the spark is reduced when the capacitor is shorted. Four curves are shown with 0Ω to 40Ω series resistors. To be intrinsically safe, the circuit must be below and to the left of the applicable curve with a 1.5 safety factor on energy. Therefore, the term intrinsically safe as used herein means a circuit which has a total capacitance which is below and to the left of the well-known applicable curve with a 1.5 safety factor on energy for a given operating voltage.

Figure 2:
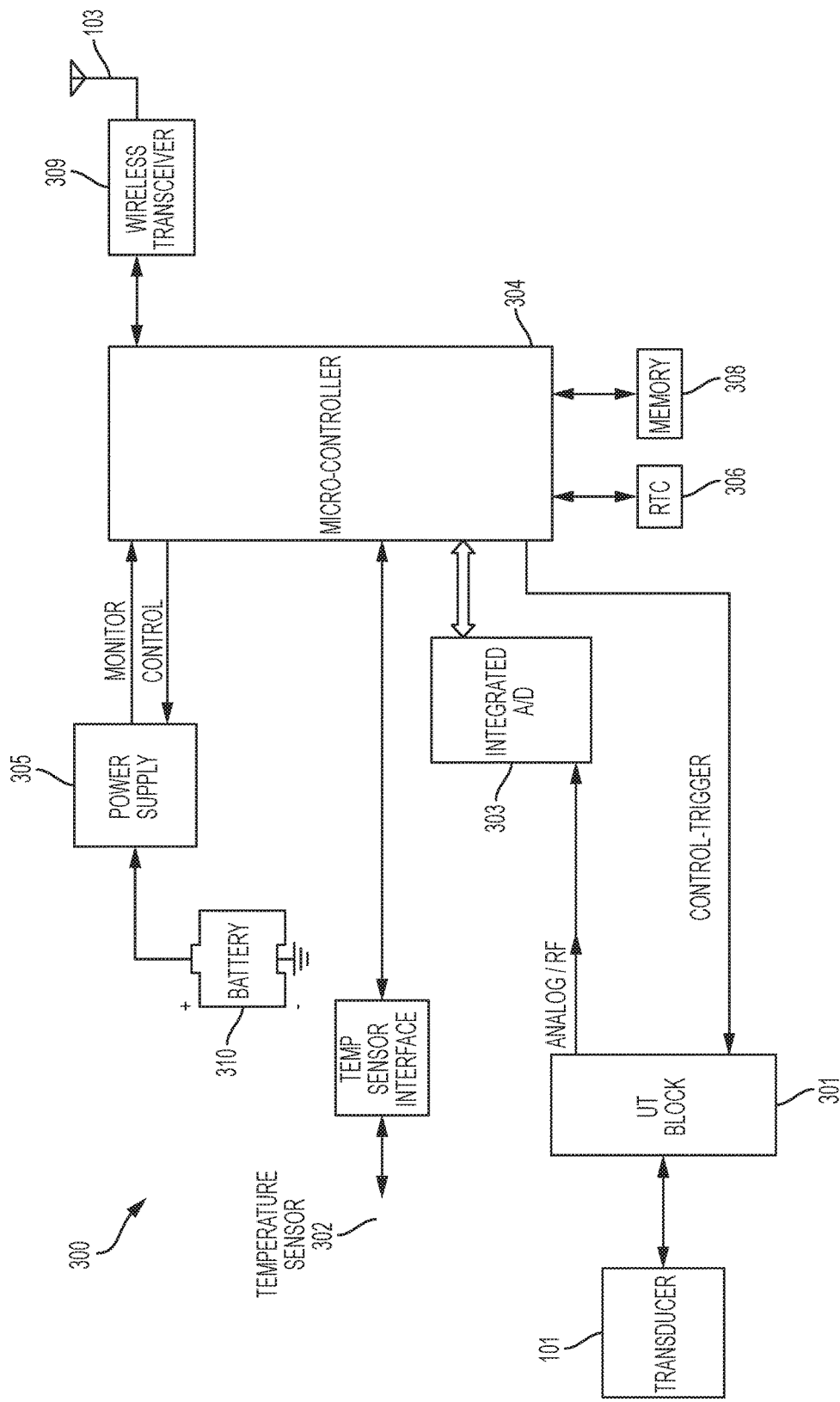
FIG. 2 shows a block diagram of one embodiment of a DSI integrated with a transducer of the present invention.

Referring to FIG. 2, a block diagram of a specific embodiment of the transducer 101 integrated with a DSI 300 into a small form factor sensor 100 (see FIG. 1). In one embodiment, the DSI comprises a transmit and receive circuitry in the form of a UT Block 301, which includes a pulser circuit to excite the ultrasonic transducer and a receiver circuit composed of one or more voltage controlled amplifiers (VCA) to amplify and condition the received signal prior to digitization. Additionally, analog filter circuits such as a low pass anti-aliasing filter and high pass filter may be included. A trigger circuit is provided from the microcontroller to fire the pulser. The microcontroller governs the timing of trigger pulses and implements the aforementioned ETS scheme. The UT pulser is either constructed to produce a low voltage square wave excitation or is designed as a "ring up" type of pulser to produce a higher voltage excitation. The receiver circuit contains one or more stages of amplification and attenuation to appropriately size the incoming voltage waveform prior to digitization. The receiver section may also contain analog filters to condition the signal and may implement highpass, low pass or band pass filters.

The analog signal from the UT block 301 feeds into an A/D converter 303, which, in one embodiment, is integrated into the processor 304, to convert the analog voltage waveform to a digital signal. The raw data as well as other outputs and/or results are then sent to an attached microcontroller 304. The microcontroller serves to manage operation of the DSI including power management through activating the various blocks of the circuit when needed.

A wireless transceiver 309 is either integrated within the MCU or is provided as a separate module to provide the functionality of data transmission. The transceiver can be implemented with known wireless communication technologies including, for example, ISA100, WirelessHART, LORA, Wi-Fi, cellular, telemetry, Blue Tooth, Blue Tooth Low Energy, ZigBee, Z-wave, and any other known wireless communication technology. It is particularly advantageous to use a technology such as LORA which has a long range, star topology as the device and radio can maintain a low-power state at all times that the individual device is not being required to measure and transmit as opposed to a mesh network where the transceiver must always be in a state where it is prepared to relay messages from other devices. The transceiver is connected to an antenna that is either internally or externally mounted to the device, or alternatively the antenna connection is routed to an external RF connector for attachment to a remote antenna. The use of a remote antenna can be advantageous for difficult RF environments.

Additionally, in one embodiment the DSI also comprises various peripheral components to the microprocessor, including, for example, a Real Time Clock 306, temperature sensor interface 307, and serial EEPROM memory 308.

Because of the sensor's modularity, the process for converting the A-scan signal to thickness data can be performed anywhere in the sensor or outside the sensor (e.g., in the Cloud or discrete device that is wireless connected to the sensor). For example, the DSI can be configured to generate the thickness data from the A-scan signal, or, alternatively, the sensor may transmit the information for processing elsewhere. Generally, determining when and where to calculate the thickness data from the A-scan signal is a question of optimization. For example, it may be preferable to convert the A-scan signal to thickness data in the DSI to save on storage space/transmission energy because the A-scan signal data consumes more space than the thickness data. On the other hand, converting this signal to thickness data tends to require more processing power. Generally, although not necessarily, sophisticated calculations such as phased array, full matrix capture, and total focusing method calculations and/or data analysis tends to be better suited for implementation in the cloud. In addition, a cloud based service is well suited to calculating and communicating alarms derived from the inspection results through media such as text messaging or email.

In one embodiment, the transceiver transmits the A-scan signal or similar signal in essentially "raw" form, along with the derived wall thickness data. For example, the A scan can be sent periodically (e.g., every 5th reading) for validation purposes, and/or upon an event (e.g. substantial change in results), again for validation.

In one embodiment, the processor is instructed to configured to place the sensor in a low-power state between readings. In one embodiment, the processor is instructed to wake up from a low power state to initiate measure of the structure on a predetermined interval. For example, in one embodiment, the predetermined interval is between 1 minute and 1 year.

In one embodiment, the data signal is transmitted to a discrete wireless collection device. In one embodiment, the wireless collection device comprises a wireless gateway that is connected to a Local Area Network (LAN). In one embodiment, the gateway transmits the data signal across the LAN to a local server. Alternatively, in one embodiment, the gateway transmits the data signal across the LAN to a remote data server. In one embodiment, the server (local or remote) hosts a data viewing application. In one embodiment, the wireless collection device stores the data signal until the data signal is collected using a handheld data collection device. In one embodiment, the handheld data collection device is connected to the wireless data collection device using a cable or over a wireless link such as Wi-Fi or Bluetooth.

In light of the description above, it should be clear to one of skill in the art that the sensor of the present invention may have a variety of features, including, for example, one or more (e.g., two or more; three or more, four or more) of the following features in each possible combination:

1. An ultrasonic transducer (101) for transmitting/receiving ultrasonic waves into and from the structure under test 2. An electrical circuit (300), with extremely short (<100 mm) or non-existent internal cables for operating the transducer, digitizing and processing the signal, and transmitting the information via an integrated wireless transceiver.

3. An integral RTD (302) or other temperature measuring sensor and circuit.

4. Software for controlling the device and collecting and processing the ultrasonic data, including a scheme of time equivalent sampling for digitizing the UT waveform.

5. A small battery (310), such as a AA Lithium or $\tfrac{2}{3}^{rd}$ AA Lithium cell to power the device for a decade, more or less depending on measurement frequency.

6. A mechanical housing (102, 104), encompassing the entire device.

7. An antenna (103) for transmitting digitized wireless RF signals.

8. A low-power wireless transceiver (309) configured in a long-range star network topology such as LORA, or as provided by OnRamp wireless or LinkLABS 9. An integrated magnet (105) or threaded mechanical fixture in the device base (104) for attachment to a metallic structure.

10. A circuitry within the housing that is intrinsically safe.

Having thus described a few particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A sensor for ultrasonically measuring a portion of a structure, said sensor comprising:
    a transducer for converting an analog transmit signal to an ultrasonic transmit signal, and for converting an ultrasonic reflected signal to an analog reflected signal;
    a housing integrated with said transducer, and comprising a mechanism for securing the sensor to said structure, said housing containing at least:
        a processor;
        a transmit and receive circuit for transmitting an analog transmit signal to said transducer in response to a transmit trigger from said processor, and for receiving an analog reflected signal from said transducer;
        an A/D converter for digitizing only a portion of said analog reflected signal in response to a sample trigger from said processor;
        a wireless data transmitter for transmitting wirelessly a data signal from said processor;
        a battery to supply power to said processor, said wireless data transmitter, said transmit and receive circuit, and said A/D converter;
        memory operatively connected to said processor and configured to instruct said processor to execute the following steps:
            repeatedly triggering said transmit and receive circuit and said A/D converter to obtain a digitized composite signal through time-equivalent sampling;

processing said digitized composite reflected signal to generate an A-scan signal; and
wirelessly transmitting said data signal based on said A-scan signal for transmission to a discrete collection device.

2. The sensor of claim 1, wherein said A/D converted is integrated with said processor.

3. The sensor of claim 2, wherein said sensor does not comprise a discrete A/D converter and a field programmable gate array (FPGA).

4. The sensor of claim 3, wherein said A/D converter and said processor are integrated on a common chip.

5. The sensor of claim 3, wherein said sensor is characterized by a total capacitance, wherein said total capacitance is lower than a sensor having a discrete A/D converter and a FPGA.

6. The sensor of claim 3, wherein said housing is characterized by a total capacitance and operating voltage, which qualifies as being intrinsically safe.

7. The sensor of claim 1, wherein said processor is instructed to configure said sensor in a low-power state between readings.

8. The sensor of claim 7, wherein said processor is instructed to wake up from a low power state to measure said structure on a predetermined interval.

9. The sensor of claim 1, further comprising a wireless collection device for receiving said data signal.

10. The system of claim 9, wherein said wireless collection device comprises a wireless gateway that is connected to a Local Area Network (LAN) and subsequently forwards said data.

11. The system of claim 10, wherein said gateway transmits said data signal across said LAN to at least one of a local server or a remote data server.

12. The system of claim 9, wherein said wireless collection device stores said data signal.

13. The system of claim 12, wherein said wireless collection device stores said data signal until said data signal is collected using a handheld data collection device.

14. The system of claim 13, wherein said handheld data collection device is at least one of a tablet computer, a laptop computer, or a smart phone.

15. A method of ultrasonically measuring a portion of a structure using a sensor comprising a transducer for converting an analog transmit signal to an ultrasonic transmit signal and for converting an ultrasonic reflected signal to an analog reflected signal, a transmit and receive circuit for transmitting an analog transmit signal to said transducer in response to a transmit trigger from a processor, and for receiving an analog reflected signal from said transducer, and an A/D converter integrated with said processor for digitizing only a sample of said analog reflected signal in response to a sample trigger form said processor, said method comprising:
permanently installing said sensor on said structure such that the position of said sensor relative to said structure is fixed;
repeatedly triggering said transmit circuit and said A/D converter while said sensor's position to said structure remains fixed to obtain a digitized composite signal through time-equivalent sampling;
processing said digitized composite reflected signal to generate an A-scan signal; and
wirelessly transmitting said data signal based on said A-scan signal to said transmitted for transmission to a discrete device.

16. The sensor of claim 15, wherein said A/D converted is integrated with said processor.

17. The sensor of claim 16, wherein said sensor does not comprise a discrete A/D converter and a field programmable gate array (FPGA).

18. The sensor of claim 15, wherein said repeatedly triggering comprises: repeatedly triggering said transmit circuit to transmit a plurality of sequential analog transmit signals to said ultrasonic transducer; repeatedly triggering said A/D converter to digital a sample of a plurality of sequential reflected signals corresponding to said plurality of sequential transmit signals; wherein either the repeated transmit triggers or the repeated converter triggers are delayed a predetermined time.

19. The method of claim 18, wherein each sequential transmit signal is delayed by said predetermined time.

20. The method of claim 19, wherein said A/D converter is configured for X samples per second (SPS), and said composite signal comprises an effective sampling rate of X samples per second, wherein Y is greater than X.

21. The method of claim 20, wherein said analog reflected signal has a frequency of F Hz, and wherein Y is at least 2 times F.

22. A sensor for ultrasonically measuring a portion of a structure, said sensor comprising:
a transducer for converting an analog transmit signal to an ultrasonic transmit signal, and for converting an ultrasonic reflected signal to an analog reflected signal;
a housing connected to said transducer;
a connection mechanism for permanently installing said transductor on said structure;
electrical components contained within said housing, said electrical components comprising at least: a processor having an integrated A/D converter and configured for Equivalent-Time Sampling (ETS) analog reflected signals from said transducer to obtain a digitized composite signal, processing said digitized composite reflected signal to generate an A-scan signal; and transmitting said data signal based on said A-scan signal, wherein said electrical components do not comprise a discrete A/D converter or a field programmable gate array (FPGA).

23. The sensor of claim 22, wherein said sensor is characterized by a total capacitance, wherein said total capacitance is lower than a sensor having a discrete A/D converter and a FPGA.

24. The sensor of claim 22, wherein said electrical components have a total capacitance and operating voltage, which qualifies as being intrinsically safe.

* * * * *